United States Patent
Fagundes

(10) Patent No.: US 8,136,175 B1
(45) Date of Patent: Mar. 20, 2012

(54) DEVICE FOR FECES COLLECTION

(76) Inventor: Ana Carolina Yoshimatsu Fagundes, São Paulo (BR)

(*) Notice: Subject to any disclaimer, the term of this patent is extended or adjusted under 35 U.S.C. 154(b) by 0 days.

(21) Appl. No.: 12/924,520

(22) Filed: Sep. 29, 2010

(51) Int. Cl.
- *A61M 1/00* (2006.01)
- *G01N 15/06* (2006.01)
- *A47K 11/04* (2006.01)
- *A47K 11/06* (2006.01)

(52) U.S. Cl. ............... 4/479; 4/484; 604/317; 422/68.1

(58) Field of Classification Search .............. 4/479–484, 4/315, 314, DIG. 18; 604/317
See application file for complete search history.

(56) References Cited

U.S. PATENT DOCUMENTS

| | | | | |
|---|---|---|---|---|
| 3,588,921 A | * | 6/1971 | Nagel | 4/245.4 |
| 3,906,555 A | * | 9/1975 | Scott et al. | 4/451 |
| 6,415,455 B1 | * | 7/2002 | Slaon et al. | 4/315 |

FOREIGN PATENT DOCUMENTS

DE    2906560 A  *  8/1980

* cited by examiner

*Primary Examiner* — Huyen Le
*Assistant Examiner* — Erin Deery
(74) *Attorney, Agent, or Firm* — Collard & Roe, P.C.

(57) ABSTRACT

A device for the collection of feces samples for laboratory diagnostic tests includes an upper layer and a lower layer, both with a semicircular or rectangular front end, and a rectilinear extension that extends toward the rear end. The upper layer has a round opening close to the front end. The lower layer has a plurality of small holes concentric to the round opening in the upper layer.

2 Claims, 3 Drawing Sheets

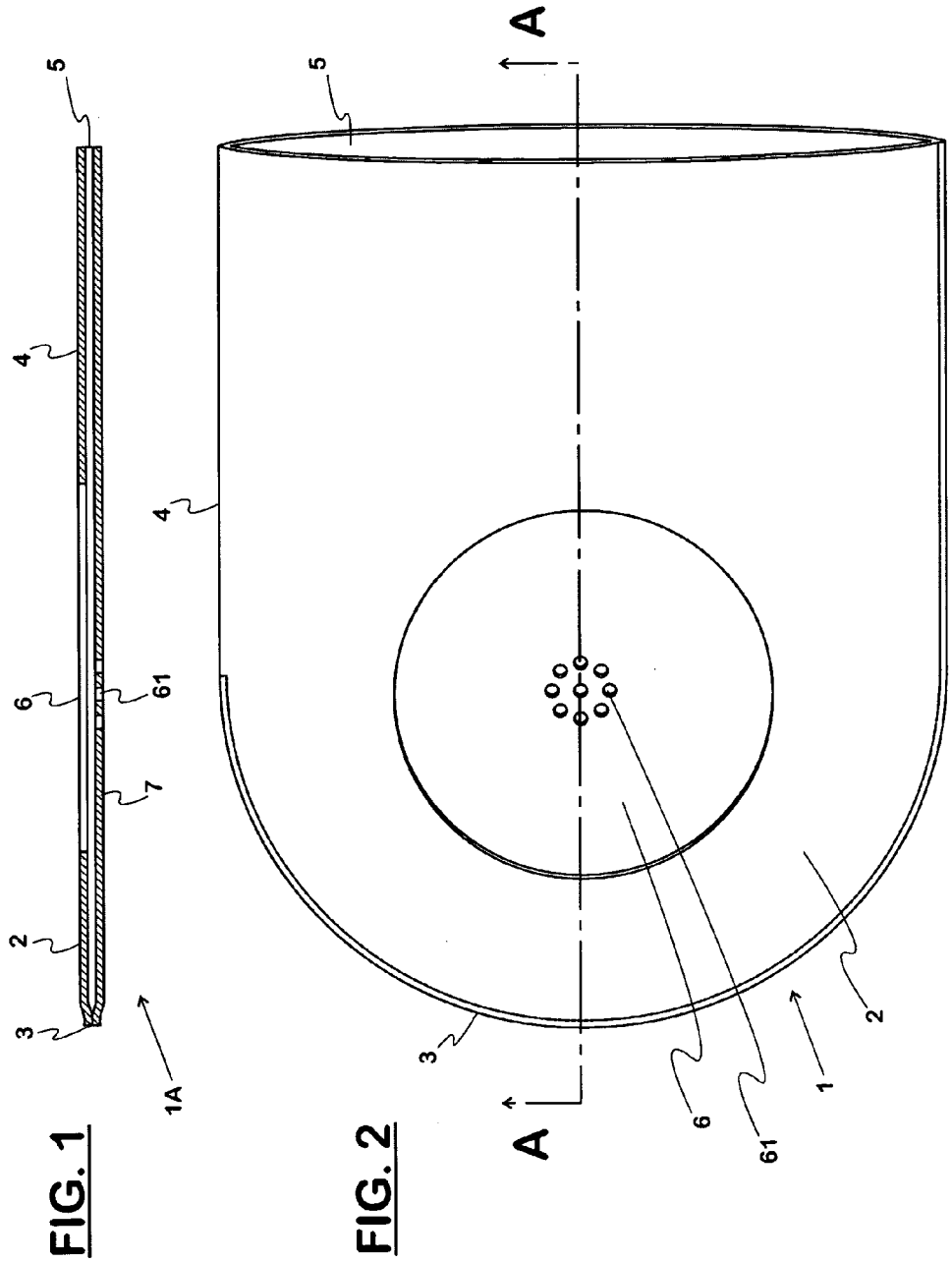

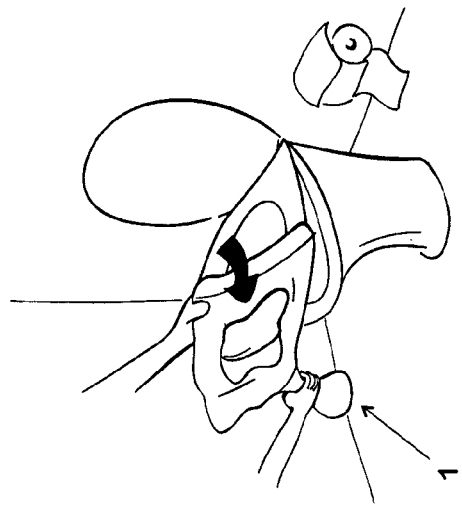
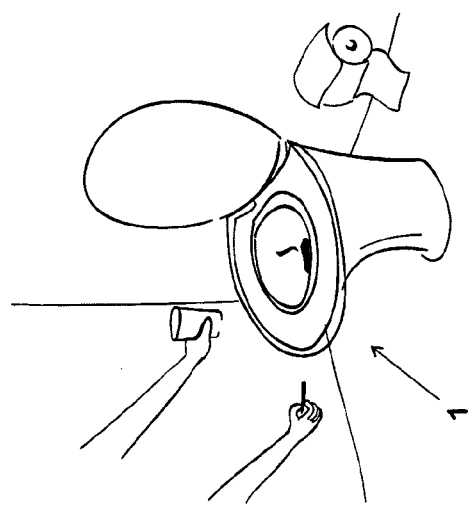
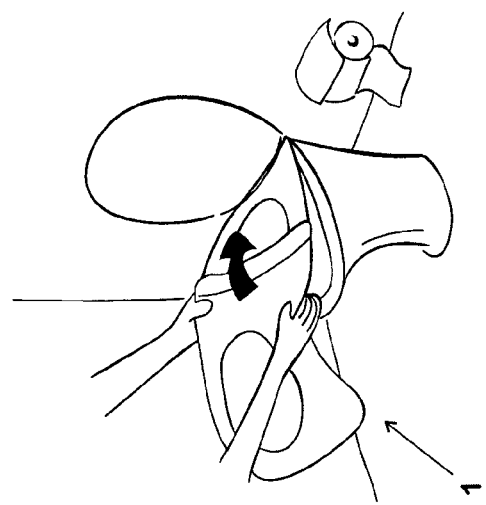

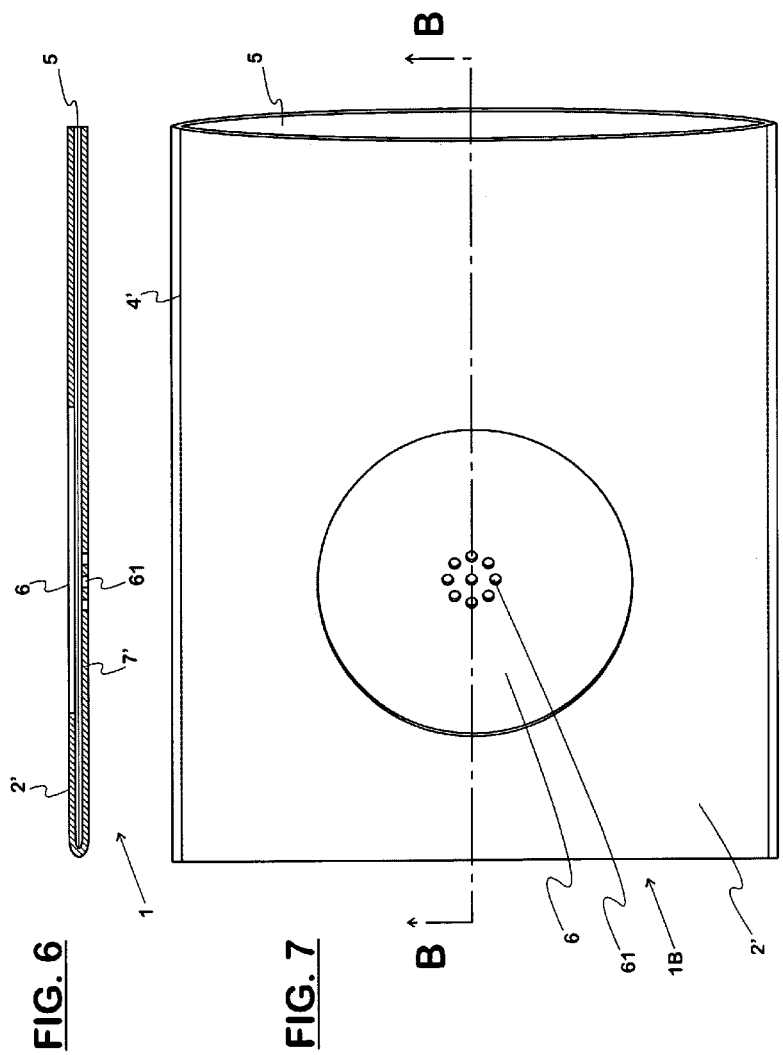

DEVICE FOR FECES COLLECTION

The present invention is for use by patients in clinical analysis laboratories, health centers, hospitals, and geriatric or pediatric clinics. In addition, the present invention is designed to be a disposable and biodegradable product. It was also conceived to assist individuals with special needs who, for some reason, face difficulties and discomfort during the process of fecal sample collection, in particular, elderly people, children, and disabled people.

The present invention is for use by patients in clinical analysis laboratories, health centers, hospitals, geriatric or pediatric clinics. In addition the present invention is designed to be a disposable and biodegradable product. It was conceived to complement the collection of individuals with special needs who, for some reason, face difficulties and discomfort at the moment of collection, especially the elders, children and the physically disabled.

It provides comfort and hygiene, avoiding embarrassing situations and mainly contamination of collected residues.

PRIOR ART

The collectors currently used consist mainly of a sterilized container, in which the patient must dispose the feces sample to be submitted to laboratory analysis, and there is also a lack of adequate auxiliary means to help the patient to collect the material safely, without contaminating the sample to be analyzed. The inconvenience is aggravated with children, the elderly people and the physically disabled that face difficulties as they need to assume uncomfortable positions.

In the face of these inconveniences, the present invention was developed to help the patient at the moment of collection.

BRIEF DESCRIPTION OF THE DRAWINGS

The present invention will be further explained in details with the accompanying drawings, where:

FIG. 1 illustrates a cross sectional view of the auxiliary device for collection (1), object of the present invention;

FIG. 2 illustrates a top view of the auxiliary device for collection (1) of the present invention;

FIG. 3 illustrates a schematic perspective view, showing the placing of the auxiliary device for collection (1) in the toilet seat;

FIG. 4 illustrates a schematic perspective view, showing the collection of the sample by the user, removed with the auxiliary device for collection (1);

FIG. 5 illustrates a schematic perspective view, showing the removal of the auxiliary device for collection (1) of the toilet seat.

FIG. 6 illustrates a schematic a cross sectional view, showing a preferred construction of the auxiliary device for collection, according to this application; and FIG. 7 illustrates a top view of a variation of a preferred construction of the auxiliary device for collection (1), according to this application.

DETAILED DESCRIPTION OF THE INVENTION

According to FIGS. 1 and 2, the auxiliary device for collection (1) includes an upper layer (2) of semicircular format in its front end (3) with a rectilinear extension (4) that extends toward the rear end (5) of the auxiliary device (1). The auxiliary device for collection (1) has a round opening (6) in the upper layer (2) close to the semicircular front end (3).

The use of the auxiliary device for collection (1) consists of covering the toilet seat with the device through the opening of the rear end (5), in a way that the round opening (6) faces the upper part of the toilet seat (FIG. 3). This allows the individual, in a practical way, to comfortably use the auxiliary device for collection (1). The material to be collected for further analysis will be deposited over the lower layer (7). Excess liquid then flows to the small holes (61) which are arranged in a way to allow the excess liquid to be drained. Then a fecal sample may be collected through the round opening (6) with a small spoon or spatula which is provided with a separate collection container.

The material preferably employed for the manufacture of the auxiliary device for collection (1) is high-density polyethylene (HDPE), however, other materials with similar characteristics may be used. The upper layer (2) is attached to the lower layer (7) by their outer peripheral edges, through conventional processes of welding. The rear end edges (5) of both layers are not attached by welding. This way, a covering with a rounded front end (3) with a rectilinear extension (4) in the rear part and with an opening in the rear end (5), which consists in the auxiliary device for collection of feces (1), is obtained.

The use of the auxiliary device for collection (1) consists of covering the toilet seat with the device through the opening of the rear end (5), in a way that the opening (6) faces the upper part of the toilet seat (FIG. 3). This allows the individual, in a practical way to comfortably use the auxiliary device for collection (1), as the material to be collected for further analysis will be deposited over upper layer (2) without the liquid, that flows away through the small holes (61) disposed in a way to allow the excess liquid to be drained off, thus letting the collection of a small sample through the opening (6), by means of a spatula or spoon provided with the universal collecting container destined to retain the sample for analysis (FIG. 4).

In a functional way, the remaining feces can be discarded in the toilet or removed with the auxiliary device (1) that will be thrown away or discarded in an appropriate excrement collecting container (FIG. 5).

According to FIGS. 6 and 7, in an alternative construction, the auxiliary device for collection (1) has a upper layer (2') attached to the lower layer (7'), both in a rectangular shape, by their outer peripheral edges (4'), through conventional processes of welding, excepting the rear end edges (5) of both layers (2' and 7').

It is evident that the auxiliary device for collection (1) proposed in the present invention provides a better application both in its use and manufacture, as it is an easy-to-use and low cost article. In addition, the auxiliary device for collection (1) is provided after sterilization, which will certainly allow the collection of samples free from contaminants that could interfere with the tests outcomes.

What is claimed is:

1. An auxiliary device for feces collection, comprising:
   an upper layer with a semicircular front end, a rectilinear extension that extends toward a rear edge, and a round opening adjacent the semicircular front end;
   a lower layer having a semicircular front end, a rectilinear extension that extends toward a rear edge and a plurality of holes concentric to the round opening in the upper layer,
   wherein the upper layer is attached to the lower layer by their outer peripheral edges through welding, and wherein the rear edges of both layers remain unattached.

2. An auxiliary device for feces collection, comprising:
a rectangular upper layer having a front end, a rear edge and a round opening adjacent the front end;
a rectangular lower layer having a front end, a rear edge and a plurality of holes concentric to the round opening in the upper layer,
wherein the upper layer is attached to the lower layer by their outer peripheral edges through welding, and
wherein the rear edges of both layers remain unattached.

\* \* \* \* \*